United States Patent
Suda et al.

(10) Patent No.: US 8,097,136 B2
(45) Date of Patent: Jan. 17, 2012

(54) HYDROGEN GAS SENSOR

(75) Inventors: Tsuyoshi Suda, Niigata (JP); Shuji Harada, Niigata (JP)

(73) Assignee: Niigata TLO Corporation, Niigata (JP)

(*) Notice: Subject to any disclaimer, the term of this patent is extended or adjusted under 35 U.S.C. 154(b) by 977 days.

(21) Appl. No.: 10/534,644

(22) PCT Filed: Feb. 18, 2005

(86) PCT No.: PCT/JP2005/002642
§ 371 (c)(1), (2), (4) Date: Apr. 6, 2006

(87) PCT Pub. No.: WO2005/080957
PCT Pub. Date: Sep. 1, 2005

(65) Prior Publication Data
US 2006/0185979 A1    Aug. 24, 2006

(30) Foreign Application Priority Data
Feb. 19, 2004 (JP) ................................ 2004-043282

(51) Int. Cl.
*G01N 27/407* (2006.01)
(52) U.S. Cl. ........................ 204/424; 204/431
(58) Field of Classification Search .............. 204/410, 204/431, 432, 424
See application file for complete search history.

(56) References Cited

U.S. PATENT DOCUMENTS

| | | | |
|---|---|---|---|
| 4,024,036 A * | 5/1977 | Nakamura et al. | 204/266 |
| 4,390,869 A * | 6/1983 | Christen et al. | 340/632 |
| 4,611,211 A | 9/1986 | Leitl et al. | |
| 4,661,211 A | 4/1987 | Petty-Weeks | |
| 4,699,509 A * | 10/1987 | Kamiya et al. | 356/70 |
| 4,704,536 A * | 11/1987 | Sugiyama et al. | 250/381 |
| 5,766,433 A | 6/1998 | Can et al. | |
| 5,935,398 A * | 8/1999 | Taniguchi et al. | 204/424 |
| 6,656,336 B2 * | 12/2003 | Mukundan et al. | 204/424 |
| 2002/0000228 A1 * | 1/2002 | Schoeb | 128/204.19 |
| 2002/0070109 A1 * | 6/2002 | Taniguchi | 204/426 |
| 2003/0024813 A1 * | 2/2003 | Taniguchi | 204/424 |
| 2004/0026268 A1 * | 2/2004 | Maki et al. | 205/784 |

FOREIGN PATENT DOCUMENTS

CA    2507428    8/2005

(Continued)

OTHER PUBLICATIONS

Shuzi Harada and Shigeru Tamaki, "EMF Measurements on Hydrogenated Palladium Alloys and Their Thermodynamic Properties", Journal of the Physical Society of Japan, Apr. 1985, pp. 1642-1647, vol. 54, No. 4.

(Continued)

*Primary Examiner* — Kaj K Olsen
(74) *Attorney, Agent, or Firm* — Greenberg Traurig, LLP

(57) ABSTRACT

A first electrode and a second electrode are provided, and an electrolyte is disposed between the first electrode and the second electrode. The first electrode and the second electrode are made of corresponding different materials in chemical potential for hydrogen gas. The first electrode includes higher chemical potential material and the second electrode includes lower chemical potential material. The first electrode functions as a detecting electrode for hydrogen gas, and the second electrode functions as a standard electrode for the hydrogen gas. The hydrogen gas is detected on an electromotive force generated between the first electrode and the second electrode.

34 Claims, 14 Drawing Sheets

FOREIGN PATENT DOCUMENTS

| | | |
|---|---|---|
| CN | 2469452 Y | 1/2002 |
| EP | 0281247 A2 | 9/1988 |
| EP | 0432840 A2 | 6/1991 |
| GB | 2128751 A | 5/1984 |
| JP | 60-007358 | 1/1985 |
| JP | 62-172256 | 7/1987 |
| JP | 63-274857 | 11/1988 |
| JP | 63-274857 A | 11/1988 |
| JP | 03-287061 | 12/1991 |
| JP | 09-236573 | 9/1997 |
| JP | 11-064275 A | 3/1999 |
| JP | 2002-214190 | 7/2002 |
| JP | 2002-214190 A | 7/2002 |
| JP | 2002-340830 | 11/2002 |
| JP | 2002-340830 A | 11/2002 |
| JP | 2003-166972 | 6/2003 |
| JP | 2003-270200 | 9/2003 |
| JP | 2003-0270200 A | 9/2003 |
| WO | WO 0189021 A1 * | 11/2001 |

OTHER PUBLICATIONS

Shuzi Harada, "Interfacial Reactions of Metal-Hydrogen Systems Measured by Electrochemical Methods", Journal of the Physical Society of Japan; vol. 58, No. 6, Jun. 1989; pp. 2200-2206.

* cited by examiner (a)

Shumitt inverter (b)

A point : input threshold voltage

US 8,097,136 B2

HYDROGEN GAS SENSOR

This application is a national stage filing under 35 U.S.C. 371 of International Application PCT/JP2005/002642, filed on Feb. 18, 2005 which claims priority from Japanese Application No: 2004-43,282 filed on Feb. 19, 2004. The entire teachings of the referenced Applications are incorporated herein by reference.

FIELD OF THE INVENTION

This invention relates to a hydrogen gas sensor which is suitable for detecting hydrogen gas leaked in air or analyzing the concentration of the hydrogen gas.

BACKGROUND OF THE ART

It is desired in a future hydrogen energy utilizing society to establish a convenient hydrogen energy system from which the hazardous nature of hydrogen explosion is removed to develop the safety of the hydrogen energy system. It is required that the hydrogen gas sensor is configured such that the hydrogen gas amount leaked in air can be detected at once and the structure of the hydrogen gas sensor can be simplified, and the reliability of the hydrogen gas sensor can be enhanced.

A conventional hydrogen gas sensor is configured on the detecting principle of semiconductor type, ionization type or combustion type, wherein the hydrogen amount is detected indirectly by utilizing the carrier concentration (semiconductor type), the ion concentration (ionization type) or the reaction heat (combustion type, or the hydrogen gas is burned to measure the vapor pressure) which can be defined as an extensive physical value, thereby to be converted into the corresponding electric value. With the conventional hydrogen gas sensor, therefore, it takes longer period of time to detect the hydrogen gas, e.g., by 100 seconds. Particularly, with a hydrogen gas sensor which is to be utilized in a hydrogen leak alarm system, it is required that the hydrogen gas sensor is configured so as to detect the hydrogen gas concentration within a low concentration range below the explosion limit and shorten the period of time in hydrogen detection.

With the conventional (semiconductor type, ionization type or combustion type) hydrogen gas sensor, since the hydrogen gas concentration is detected by utilizing the carrier concentration, the ion concentration or the reaction heat as a hydrogen gas detecting signal, the hydrogen detection requires a large detecting area. In this point of view, the detection precision and sensitivity of the hydrogen gas depends on the structure, the shape and the electrode size of the hydrogen gas sensor, so that the reduction in size of the hydrogen gas sensor is restricted. Moreover, the conventional (semiconductor type, ionization type or combustion type) hydrogen gas sensor may suffer from environmental gases. Particularly, when the hydrogen gas sensor is employed in the atmosphere containing gasoline, hydrocarbon and alcohol which contain hydrogen elements, the hydrogen gas sensor may respond to the hydrogen-based gases, thereby to deteriorate the reliability of the hydrogen gas detection.

In this point of view, new electrochemical gas sensors have been developed and practically used, in substitution for the above-mentioned conventional hydrogen gas sensors. The new gas sensors can be classified as electromotive force measuring type hydrogen gas sensors and current detecting type hydrogen gas sensors. With the former type hydrogen gas sensors, as disclosed in Patent Publication No. 1 and 2, a hydrogen gas electrode is prepared as a standard electrode which is configured on the hydrogen standard gas pressure, and a detecting electrode is prepared as an operating electrode for measuring the gas to be detected (hydrogen gas), wherein the difference in potential between the hydrogen gas electrode and the detecting electrode is measured as the output of the hydrogen gas sensor corresponding to the hydrogen gas concentration.

With the hydrogen electrode, the atomic hydrogen exists sufficiently on the electrode surface to form the standard potential of the electrode. Under the condition, when hydrogen gas contacts with the detecting electrode to be dissociated into atomic hydrogen, the detecting electrode exhibits an electric potential in proportion to the amount of the atomic hydrogen, and the difference in potential between the hydrogen gas electrode and the detecting electrode is detected as the function of the hydrogen gas concentration. In other words, with the new hydrogen gas sensors, since the detecting hydrogen gas pressure is measured in comparison with the standard hydrogen gas pressure, both of electrodes must be disposed independently in the standard hydrogen gas atmosphere and the detecting gas atmosphere, so that another "standard hydrogen gas pressure room must be provided in addition of the detecting gas pressure room. In this point of view, the hydrogen gas sensors are required to be enlarged in size and the use condition and the like of the hydrogen gas sensors are restricted.

With the current detecting type hydrogen gas sensors, the current value is classified as an extensive physical value, so that in order to realize a high precise measurement using the hydrogen gas sensors, the areas or the volumes of the hydrogen gas sensors must be enlarged and external power supplies can be provided for the hydrogen gas sensors.

[Patent Publication No. 1]
Japanese Patent Application Laid-open No. 2003-270200
[Patent Publication No. 2]
Japanese Patent Application Examined Publication No. 5-663

DISCLOSURE OF THE INVENTION

Problem to be Solved by the Invention

It is an object of the present invention to provide a new electromotive force type hydrogen gas sensor on electrochemical principle wherein the structure of the hydrogen gas sensor is simplified and the hydrogen gas can be detected high precisely at once.

Means for Solving the Problem

In order to achieve the object, this invention relates to a hydrogen gas sensor comprising a first electrode, a second electrode and an electrolyte contacting with the first electrode and the second electrode, wherein the first electrode and the second electrode are made of corresponding different materials in chemical potential for hydrogen gas, and the first electrode is made of higher chemical potential material and the second electrode is made of lower chemical potential material, wherein the hydrogen gas is detected on an electromotive force generated between the first electrode and the second electrode.

In the present invention, the electrodes of the hydrogen gas sensor are configured so as to contain the corresponding different materials in chemical potential from one another, and the first electrode containing the higher chemical potential material is defined as a detecting electrode and the second electrode containing the lower chemical potential material is defined as a standard electrode. Therefore, when the hydrogen gas sensor is disposed in the same atmosphere containing hydrogen gas, the difference in potential between the first electrode and the second electrode of the hydrogen gas sensor is generated because the electrodes are made of the different materials in chemical potential, respectively. As a result, the hydrogen gas under the same atmosphere can be detected from the difference in potential between the electrodes.

According to the hydrogen gas sensor of the present invention, since another standard hydrogen gas pressure room is not required different from the conventional electromotive force measuring type hydrogen gas sensor, the structure of the hydrogen gas sensor can be simplified and the size of the hydrogen gas sensor can be reduced, and also, the hydrogen gas can be detected at once.

Herein, the difference in potential between the electrodes of the hydrogen gas sensor is originated from the following relative equation $$\tilde{\mu}_H^M - \tilde{\mu}_H^{H_2} = (\tilde{\mu}_e^{II} - \tilde{\mu}_e^{I}) - F(\phi_e^{II} - \phi_e^{I}) = -FE \quad (1)$$

wherein the reference character "F" means Faraday constant, and the reference character "E" means EMF value, and $\tilde{\mu}_H^M$, $\tilde{\mu}_H^{H_2}$ are electro-chemical potentials are equal to chemical potentials, respectively of atomicity hydrogen for metal and hydrogen gas. Then, since the terminals [I] and [II] are made of the same copper wire, the electro-chemical potentials of electron are represented by the following equation:

$$\tilde{\mu}_e^{II} = \tilde{\mu}_e^{I} \quad (2)$$

Herein, the equation (3) showing the relation between the electrostatic potential and the electromotive force E is employed:

$$\phi_e^{II} - \phi_e^{I} = E \quad (3)$$

wherein $\phi^I$ means an electrostatic of the first electrode and $\phi^{II}$ means an electrostatic of the second electrode.

In this way, the hydrogen gas sensor of the present invention derives the electromotive force corresponding to the chemical potential difference originated from the atomicity hydrogen concentration for both of the electrodes, and detects the hydrogen gas concentration on the electromotive force. As mentioned above, in the present invention, the first electrode is configured as the detecting electrode such that the first electrode contains the higher chemical potential material and the second electrode is configured as the standard electrode such that the second electrode contains the lower chemical potential material, so that the electromotive force E is originated mainly from the electrostatic potential of the first electrode.

Since the electromotive force E depends only on the kinds of the electrode materials relating to the chemical potential, not on the size and structure of the electrodes, the hydrogen gas sensor can be reduced in size and simplified in structure. Moreover, since the above-mentioned reaction is created as soon as the hydrogen gas contacts with the first electrode as the detecting electrode, the hydrogen gas detection can be carried out at once.

Herein, since the hydrogen gas sensor of the present invention has an inherent spontaneous electromotive force under non-hydrogen atmosphere, the hydrogen gas sensor can have the self-diagnosed function relating to the operationality.

In the hydrogen gas sensor, the chemical potential can be associated with the absorption-dissociation active degree of hydrogen gas. That is, the hydrogen gas sensor can be configured such that the electrodes can contain the corresponding different materials in hydrogen absorption-dissociation active degree from one another. In this case, if the first electrode is made of a material of higher absorption-dissociation active degree for hydrogen gas and the second electrode is made of a material of lower absorption-dissociation active degree for hydrogen gas, the first electrode can contain the higher chemical potential material and the second electrode can contain the lower chemical potential material.

Concretely, the first electrode can contain a first electrode material which can exhibit a standard electromotive force of 0.8V or over in the cell of $H_2(-)|50$ $mol/m^3$ $H_2SO_4|sample$ (+), and the second electrode can contain a second electrode material of less than 0.8V in the same cell construction.

As the first electrode material can be exemplified Pt, Pt alloy, Pd, Pd alloy. The first electrode can be made of the above-exemplified material or a supported material of the above-exemplified material on a given substrate. The first electrode can be formed in any construction within a scope of the present invention only if the first electrode can function as the detecting electrode for hydrogen gas.

As the second electrode material can be exemplified Ni, Ni alloy, Ti, Ti alloy, Cu, Cu alloy, Fe, Fe alloy, Al, Al alloy and organic conductive material. The second electrode can be made of the above-exemplified material, but can be formed in any construction within a scope of the present invention only if the second electrode can function as the standard electrode for the hydrogen gas.

A hydrogen gas sensor wherein the detecting electrode for hydrogen gas is made of Pd—H is disclosed in Non-patent Publication No. 1. In this case, since hydrogen gas is partially evaporated from the detecting electrode with time in use, the hydrogen gas sensor can not exhibit the inherent effect/function. In contrast, in the present invention, such a hydrogen-containing electrode is not employed, the above-mentioned problem relating to the use of the hydrogen-containing electrode can be ironed out.

[Non-Patent Publication No. 1]

A. Macker et al., ASTM Spec Tech Publ. No. 962 (June 1998), p 90-97

Moreover, the electrolyte may be made of liquid electrolyte or solid electrolyte, but preferably made of the solid electrolyte. In this case, the handling of the hydrogen gas sensor can be simplified, and can be precisely operated within a temperature range of room temperature (0° C.)-120° C. If a micro heater or the like is installed in the hydrogen gas sensor, the hydrogen gas can be detected easily within a low temperature range of 0° C. or below.

As the solid electrolyte can be exemplified phosphorous tungstic acid or phosphorous molybdic acid which has good adhesion for the first electrode and the second electrode and is excellent as an electrolyte for the hydrogen gas sensor.

The phosphorous tungstic acid and the phosphorous molybdic can be obtained in the form of powder, so that in the fabrication of the solid electrolyte, the powdery phosphorous tungstic acid or phosphorous molybdic acid is pressed and molded in pellet, and then, processed into the solid electrolyte. However, the pellet is too fragile to be employed for the solid electrolyte as it is. In the use, therefore, some glass wool are added as reinforcing material into the powdery phosphorous tungstic acid or phosphorous molybdic acid in a given solvent (such as ion exchanged water), thereby to be solidified to provide the solid electrolyte. Concretely, the solid electrolyte will be made by the following steps:

(1) A powdery raw material for the intended solid electrolyte (such as phosphorous tungstic acid) is melted in a given solvent to be liquidized, (2) A reinforcing material is set into a mold for forming the solid electrolyte, (3) The liquidized raw material is flowed into the mold containing the reinforcing material, (4) The liquidized raw material is solidified to form the solid electrolyte as the primitive form of the hydrogen gas sensor.

Herein, it may be that the solid electrolyte is melted and the reinforcing material is added to the melted electrolyte, in substitution for the step (2).

In one aspect of the present invention, the hydrogen gas sensor is combined with a voltage comparator to form a hydrogen gas leak alarm system, wherein an electromotive force created on the hydrogen gas detection by the hydrogen gas sensor is compared with a reference voltage of the voltage comparator, and if the electromotive force is larger than the reference voltage, a predetermined alarm is raised.

In another aspect of the present invention, a plurality of hydrogen gas sensors are prepared, and arranged on the same substrate to form a hydrogen gas sensor array. According to the hydrogen gas sensor array, hydrogen gas leak from a pipe line series can be detected to form the hydrogen gas leak distribution. If the sensors are arranged densely in series, the sensor output voltage can be enhanced by several times.

As the solid electrolyte can be exemplified phosphorous tungsten acid or phosphorous molybdenum acid which has good adhesion for the first electrode and the second electrode and is excellent as an electrolyte for the hydrogen gas sensor.

Effect of the Invention

As described above, since the hydrogen gas sensor of the present invention is configured such that the electrodes are made of the corresponding different material in chemical potential for hydrogen gas and the hydrogen gas is detected by the difference in electromotive force between the electrodes corresponding to the difference in the chemical potential therebetween, the hydrogen gas detection can be carried out at once and the detection performance of hydrogen gas under a low hydrogen gas concentration can be enhanced. Moreover, since the chemical potential and the electromotive force are defined as extensive physical values and do not depend on the size of the electrodes, the hydrogen gas sensor of the present invention can be downsized. Also, since the hydrogen gas sensor can be disposed with the electrodes in the same atmosphere, another standard hydrogen gas pressure room is not required. Therefore, the structure of the hydrogen gas sensor can be simplified and the size of the hydrogen gas sensor can be reduced. In addition, the hydrogen gas sensor can have the inherent spontaneous electromotive force under the non-hydrogen atmosphere, the hydrogen gas sensor can have self-diagnosed function of the operationality.

PREFERRED EMBODIMENTS FOR CARRYING OUT THE INVENTION

Details, other features and advantages of the present invention will be described hereinafter, with reference to "Preferred Embodiments for Carrying out the Invention".

Figure 1:
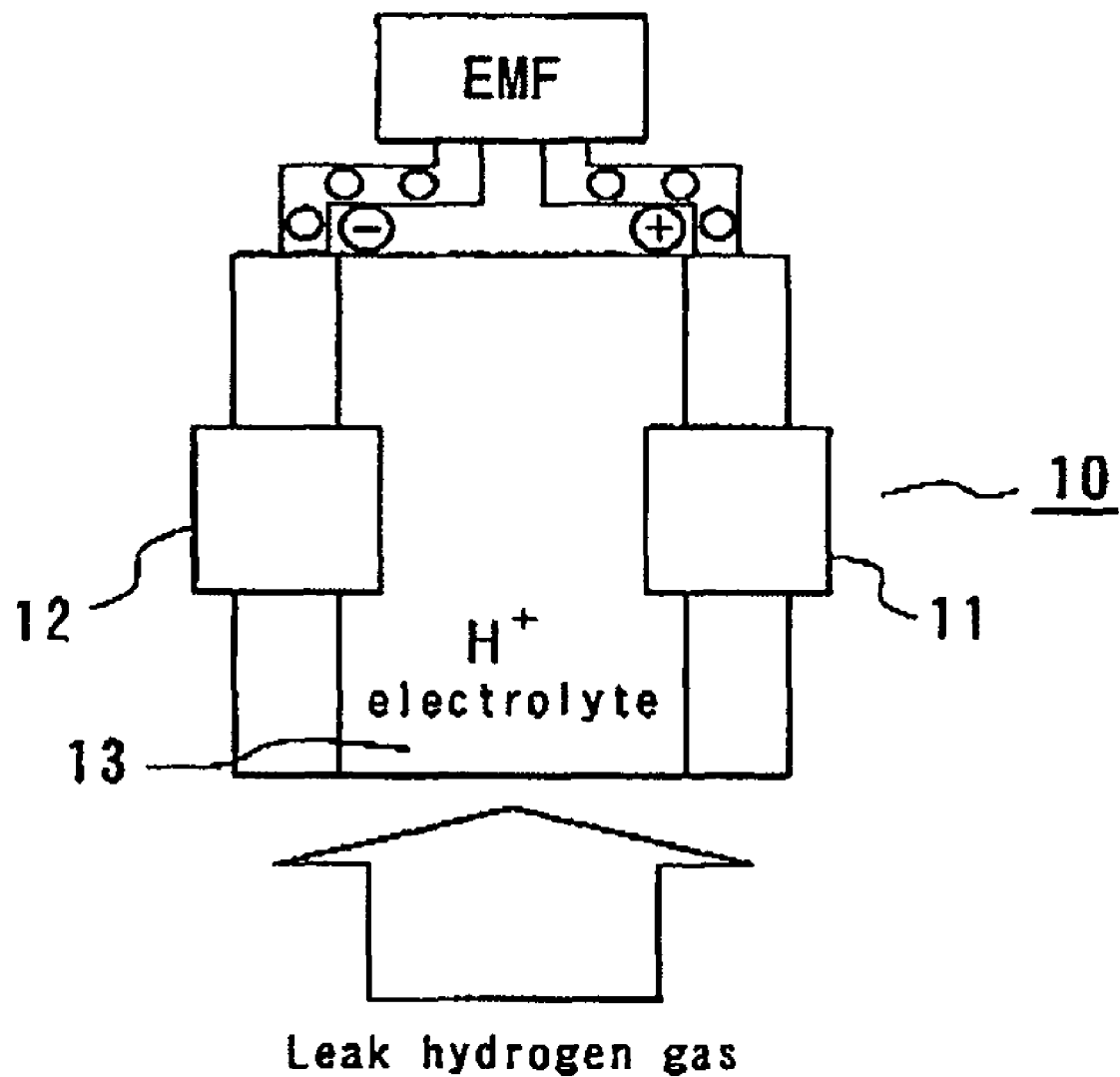
FIG. 1 is a structural view illustrating a hydrogen gas sensor according to the present invention.

FIG. 1 is a structural view illustrating a hydrogen gas sensor according to the present invention. Like or similar components are designated by the same reference numerals throughout all of the figures.

The hydrogen gas sensor 10 illustrated in FIG. 1 includes a plate-like first electrode 11 and a plate-like second electrode 12, and a solid electrolyte 13 disposed between the electrodes. The first electrode 11 functions as a detecting electrode for hydrogen gas, and the electrostatic potential of the first electrode 11 is varied remarkably when the hydrogen gas contacts with the first electrode 11. The second electrode 12 functions as a standard electrode for the hydrogen gas, and the electrostatic potential of the second electrode 12 is not almost varied or if varied, the variable degree is very small when the hydrogen gas contacts with the second electrode 12.

The first electrode 11 is made of a first electrode material of higher chemical potential such as Pt, Pt alloy, Pd, Pd alloy which are higher absorption-dissociation active degree materials. The first electrode 11 can be made of the above-exemplified material or a supported material of the above-exemplified material on a given substrate. The first electrode 11 can be formed in any construction within a scope of the present invention only if the first electrode 11 can function as the detecting electrode for hydrogen gas.

The second electrode 12 is made of a second electrode material such as Ni, Ni alloy, Ti, Ti alloy, Cu, Cu alloy, Fe, Fe alloy, Al, Al alloy and organic conductive material which are lower absorption-dissociation active degree materials. The second electrode 12 can be made of the above-exemplified material, but can be formed in any construction within a scope of the present invention only if the second electrode 12 can function as the standard electrode for the hydrogen gas.

In this embodiment, the first electrode 11 and the second electrode 12 are formed in plate, but may be formed in any shape such as linear shape, cylindrical shape, disc shape or rectangular shape.

The solid electrolyte 13 may be made of an electrolyte such as phosphorous tungstic acid which has higher adhesion for the first electrode 11 and the second electrode 12. The solid electrolyte 13 may contain reinforcing material such as glass wool in addition to the electrolyte such as phosphorous tungstic acid. In this case, the strength of the solid electrolyte 13 can be enhanced and the adhesion of the solid electrolyte 13 for the first electrode 11 and the second electrode 12 can be enhanced.

Figure 2:
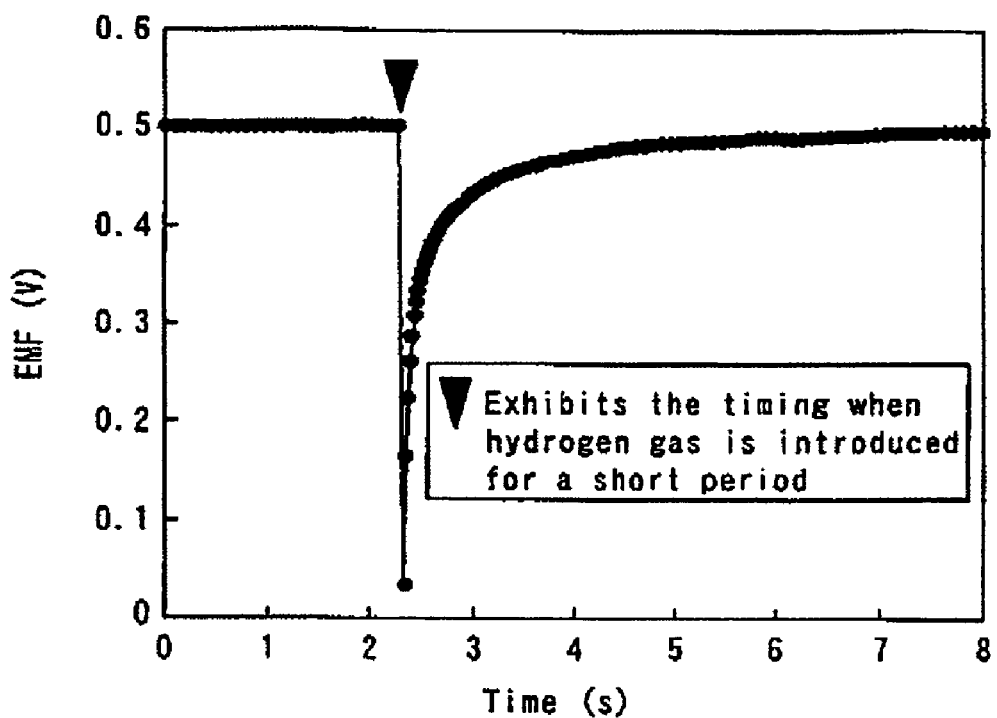
FIG. 2 is a graph showing an electromotive force between the electrodes 11 and 12 of the hydrogen gas sensor illustrated in FIG. 1 when the hydrogen gas sensor is disposed in a hydrogen-containing atmosphere.

FIG. 2 is a graph showing the variation in electromotive force generated between the electrodes 11 and 12 when the hydrogen gas sensor illustrated in FIG. 1 is disposed in a hydrogen-containing atmosphere. In this case, the first electrode 11 is made of Pt and the second electrode 12 is made of Ni. As is apparent in FIG. 2, in the hydrogen gas sensor, the electromotive force is varied (decreased) within several decimal seconds of less than one second as soon as the hydrogen gas sensor, that is, the electrodes contact with the hydrogen gas. Therefore, the hydrogen gas sensor 10 illustrated in hydrogen gas sensor can detect the hydrogen gas at once.

Figure 3:
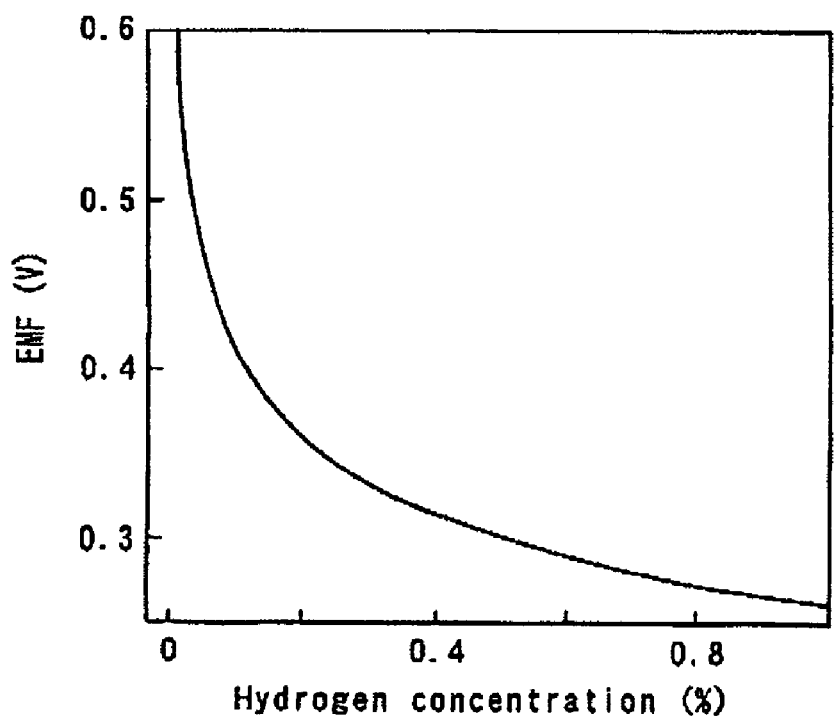
FIG. 3 is a graph showing the relation between the electrostatic potential and the hydrogen gas concentration at the first electrode of the hydrogen gas sensor illustrated in FIG. 1, FIG. 4 are structural views illustrating another hydrogen gas sensor according to the present invention, FIG. 4(a) being a top plan view of the hydrogen gas sensor, FIG. 4(b) being a side view of the hydrogen gas sensor.

FIG. 3 is a graph showing the relation between the electrostatic potential and the hydrogen gas concentration at the first electrode 11 of the hydrogen gas sensor 10 illustrated in FIG. 1. As is apparent from FIG. 3, the electrostatic potential of the first electrode 11 is decreased uniformly with the hydrogen gas concentration. In contrast, the electrostatic potential of the second electrode 12 of the hydrogen gas sensor 10 does not almost depend on the hydrogen gas concentration. Therefore, an electromotive force of the hydrogen gas sensor 10 is varied with the hydrogen gas concentration, and the hydrogen gas concentration can be detected by the variation of the electromotive force. In this case, the electromotive force of the hydrogen gas sensor is decreased with the increase of the hydrogen gas concentration.

In this point of view, the hydrogen gas sensor 10 illustrated in FIG. 1 is excellent in the hydrogen gas detection under minute hydrogen gas concentration (several decimal %).

When the environmental temperature of the hydrogen gas sensor 10 illustrated in FIG. 1 is varied within a temperature range of 0-120° C., it is confirmed that the hydrogen gas sensor 10 can operate in the hydrogen gas detection within the temperature range.

Figure 4:
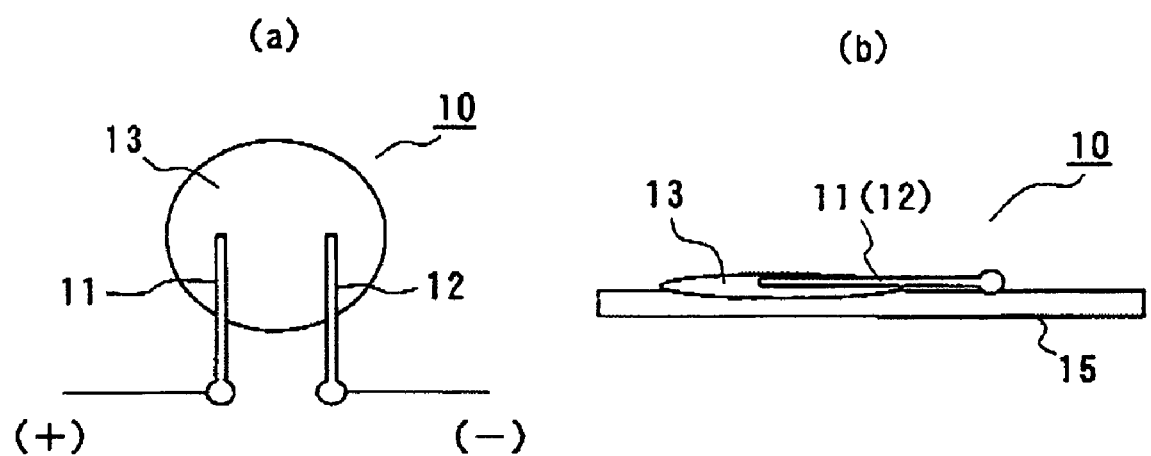

FIG. 4 is a structural view illustrating another hydrogen gas sensor according to the present invention. In the hydrogen gas sensor illustrated in FIG. 4, a wire-like first electrode 11 and a wire-like second electrode 12 are disposed on an insulating substrate 15 so as to be opposed to one another. The electrodes 11 and 12 can be made by means of sputtering and the like. A solid electrolyte 13 is provided between the first electrode 11 and the second electrode 12 on the insulating substrate 15. In this embodiment, the hydrogen gas sensor can exhibit the same effect/function as the hydrogen gas sensor relating to FIG. 1 if the first electrode 11 and the second electrode 12 are made of corresponding different materials in chemical potential.

The first electrode 11 functions as a detecting electrode and is made of higher chemical potential material, and the second electrode 12 functions as a standard electrode and is made of lower chemical potential material. Concretely, the first electrode 11 and the second electrode 12 can be made of the same materials as the corresponding electrodes of the hydrogen gas sensor relating to FIG. 1, respectively.

Figure 5:
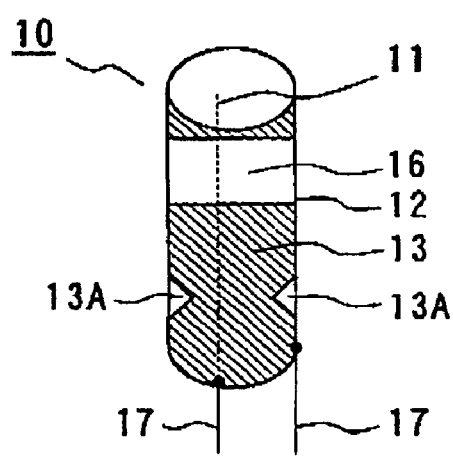
FIG. 5 is a structural view illustrating still another hydrogen gas sensor according to the present invention.

FIG. 5 is a structural view illustrating still another hydrogen gas sensor according to the present invention. In the hydrogen gas sensor 10 illustrated in FIG. 5, a first electrode member 11 and a solid electrolyte 13 are disposed in a cylindrical member 12 made of stainless steel or the like. The solid electrolyte 13 is divided substantially at the center by a gas permeable film 16 and reduced in diameter at the rear portion to form the reducing processed portion 13A. In this case, the cylindrical member 12 also functions as the second electrode corresponding to the standard electrode for the hydrogen gas. On the other hand, the first electrode member 11 functions as the detecting electrode for the hydrogen gas and is made of higher chemical potential material such as Pt.

In the hydrogen gas sensor 10 illustrated in FIG. 5, an electromotive force between the first electrode member 11 and the cylindrical member 12 is measured via wires 17 connected to the electrode materials, so that the hydrogen gas can be detected on the electromotive force.

Figure 6:
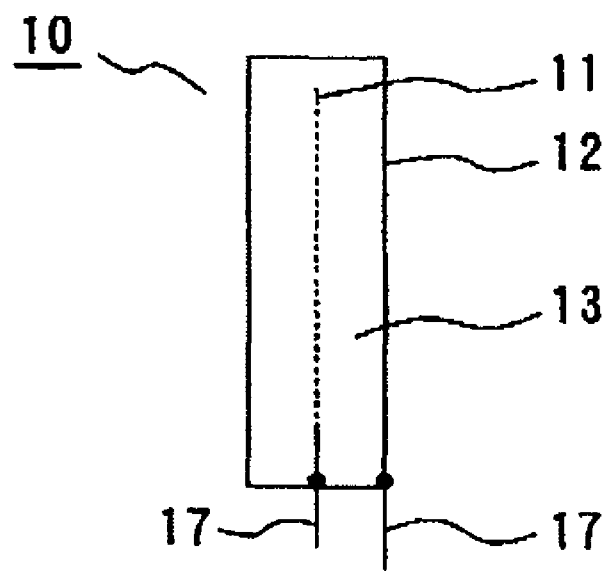
FIG. 6 is a structural view illustrating a further hydrogen gas sensor according to the present invention.

FIG. 6 is a structural view illustrating a further hydrogen gas sensor according to the present invention. In the hydrogen gas sensor 10 illustrated in FIG. 6, a first electrode 11 and a solid electrolyte 13 are disposed in a tubule 12 such as a needle. In this case, the tubule 12 functions as the second electrode corresponding to the standard electrode for hydrogen gas, and the first electrode member 11 functions as the detecting electrode for the hydrogen gas. The first electrode 11 is made of higher chemical potential material such as Pt and the second electrode member 12 is made of lower chemical potential material such as Ni.

In the hydrogen gas sensor 10 illustrated in FIG. 6, an electromotive force between the first electrode 11 and the tubule 12 is measured via wires 17 connected to the electrode materials, so that the hydrogen gas can be detected on the electromotive force.

Figure 7:
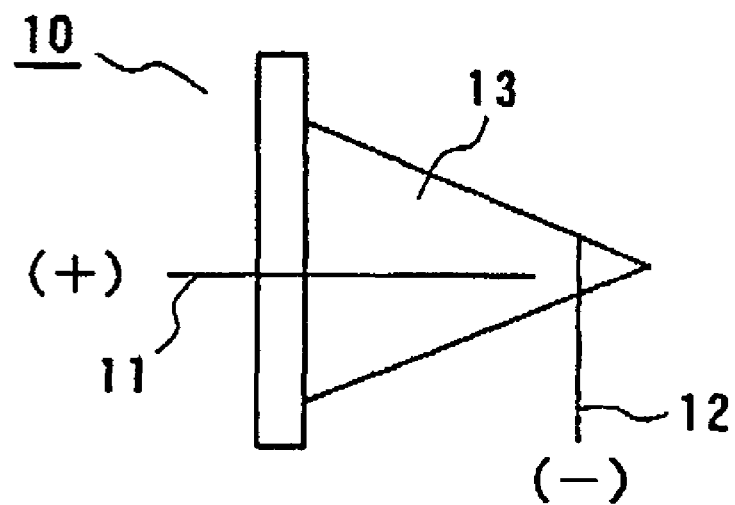
FIG. 7 is a structural view illustrating a still further hydrogen gas sensor according to the present invention.
Figure 8:
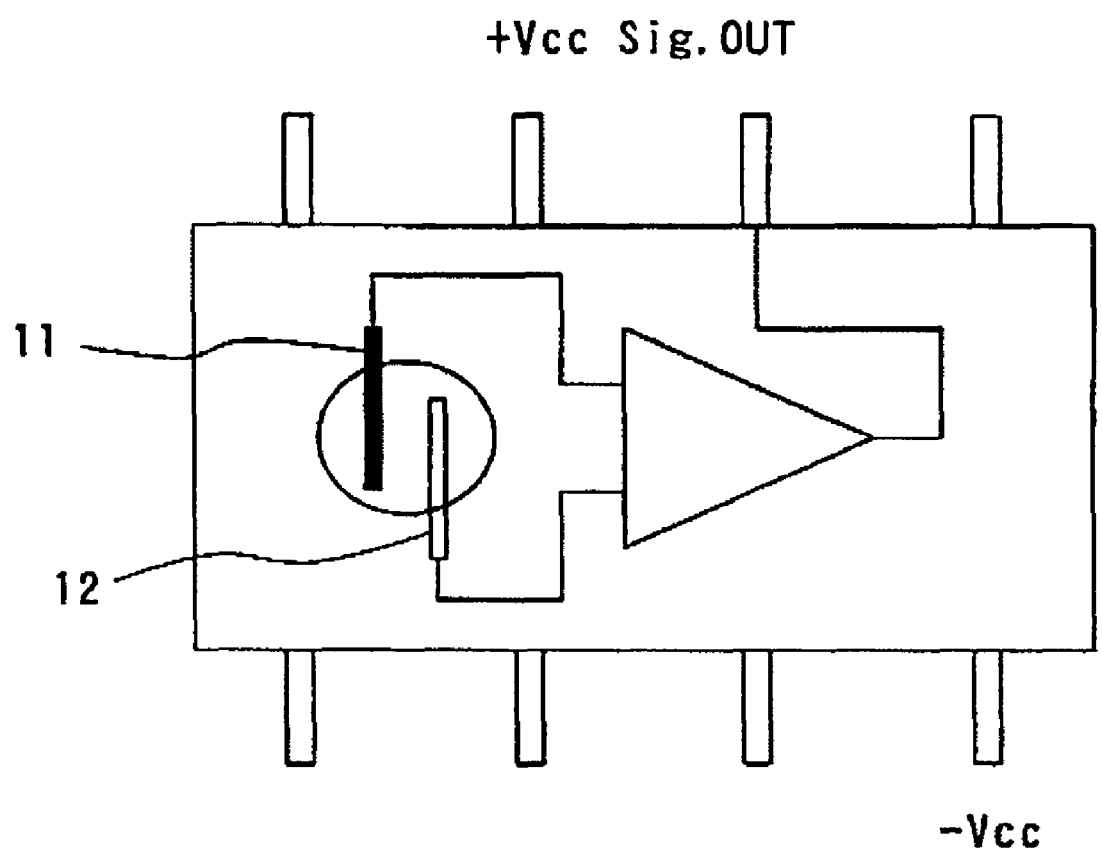
FIG. 8 is a view illustrating the state where the hydrogen gas sensor illustrated in FIG. 7 is integrated.

FIG. 7 is a structural view illustrating a still further hydrogen gas sensor according to the present invention. In the hydrogen gas sensor 10 illustrated in FIG. 7, a tapping screw 12 constitutes the second electrode and a solid electrolyte 13 is charged into the tapping screw 12, and a first electrode 11 is inserted into the tapping screw 12. In this case, hydrogen gas can be detected on an electromotive force generated between the first electrode 11 and the second electrode 12. Herein, the first electrode 11 and the second electrode (tapping screw) 12 may be made of the above-mentioned different materials in chemical potential from one another. FIG. 8 is a view illustrating the state where the hydrogen gas sensor illustrated in FIG. 7 is integrated As illustrated in FIG. 5, when the second electrode is made of such a cylindrical member, the second electrode (cylindrical member) may be formed in porosity or mesh in view of the permeability of the hydrogen gas.

Figure 9:
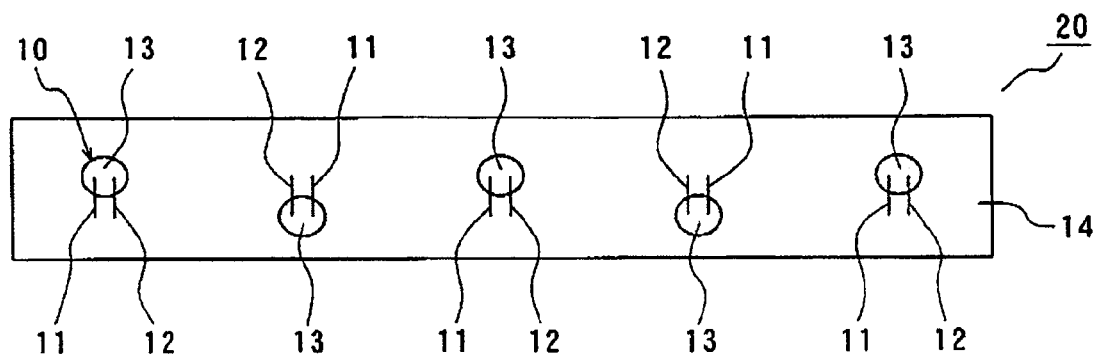
FIG. 9 is a structural view illustrating a hydrogen gas sensor array according to the present invention.

FIG. 9 is a structural view illustrating a hydrogen gas sensor array according to the present invention. In the hydrogen gas sensor array illustrated in FIG. 9, a plurality of hydrogen gas sensors according to FIG. 4 are arranged on an insulating substrate 14. In this case, since each hydrogen gas sensor can detect hydrogen gas, the array can detect the hydrogen gas depending on the detecting position. Therefore, the array is suitable for hydrogen gas leak in the wide area such as a hydrogen gas station.

If the hydrogen gas sensors are arranged in high density, the array can be constituted as a leak detector using each hydrogen gas sensor as a probe.

Figure 10:
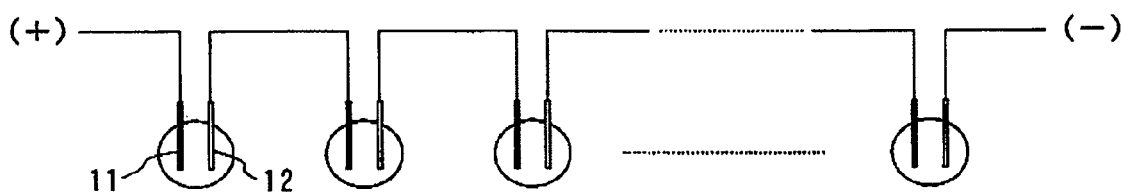
FIG. 10 is a view illustrating the state where a plurality of hydrogen gas sensors according to FIG. 7 are arranged and connected to one another in series.

In the array illustrated in FIG. 9, when the hydrogen gas sensors are connected to one another in series as illustrated in FIG. 10, the electromotive forces from the hydrogen gas sensors are added up to provide larger detecting voltage.

The hydrogen gas sensor illustrated in FIG. 1, 4-8 or the hydrogen gas sensor array illustrated in FIG. 9, 10 can be installed in a suitable electric circuit, and the detecting voltage is detected via the electric circuit. If the hydrogen gas sensor is installed into the electric circuit, the electromotive force of the hydrogen gas sensor becomes constant under non-hydrogen atmosphere, which is defined as an electrostatic potential between the first electrode and the second electrode. In this case, therefore, if the electromotive force is measured via the electric circuit, the operating reliability of the hydrogen gas sensor can be appropriately confirmed, so that the hydrogen gas sensor can have the self-diagnosed function.

Figure 11:
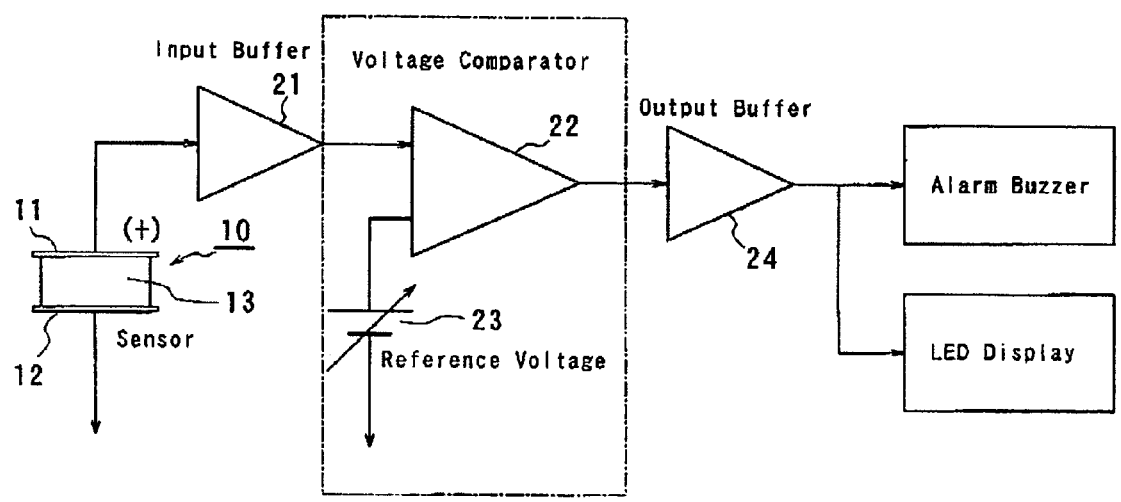
FIG. 11 is a block diagram of a hydrogen gas leak alarm system utilizing a hydrogen gas sensor according to the present invention.
Figure 12:
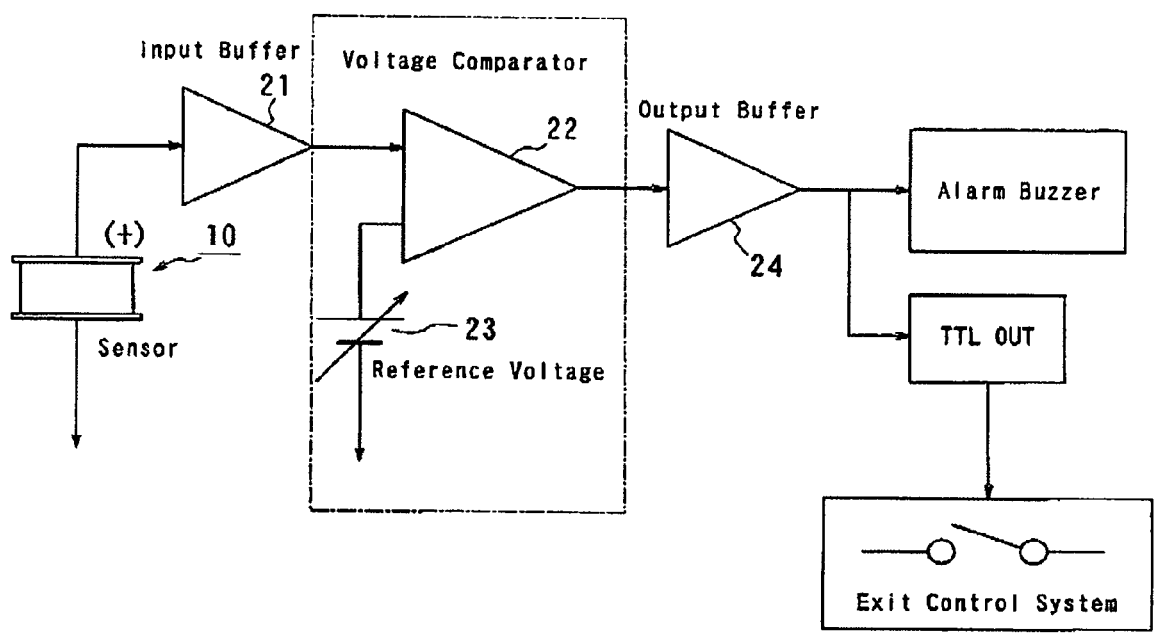
FIG. 12 is a block diagram of a hydrogen gas leak controlling system utilizing a hydrogen gas sensor according to the present invention.
Figure 13:
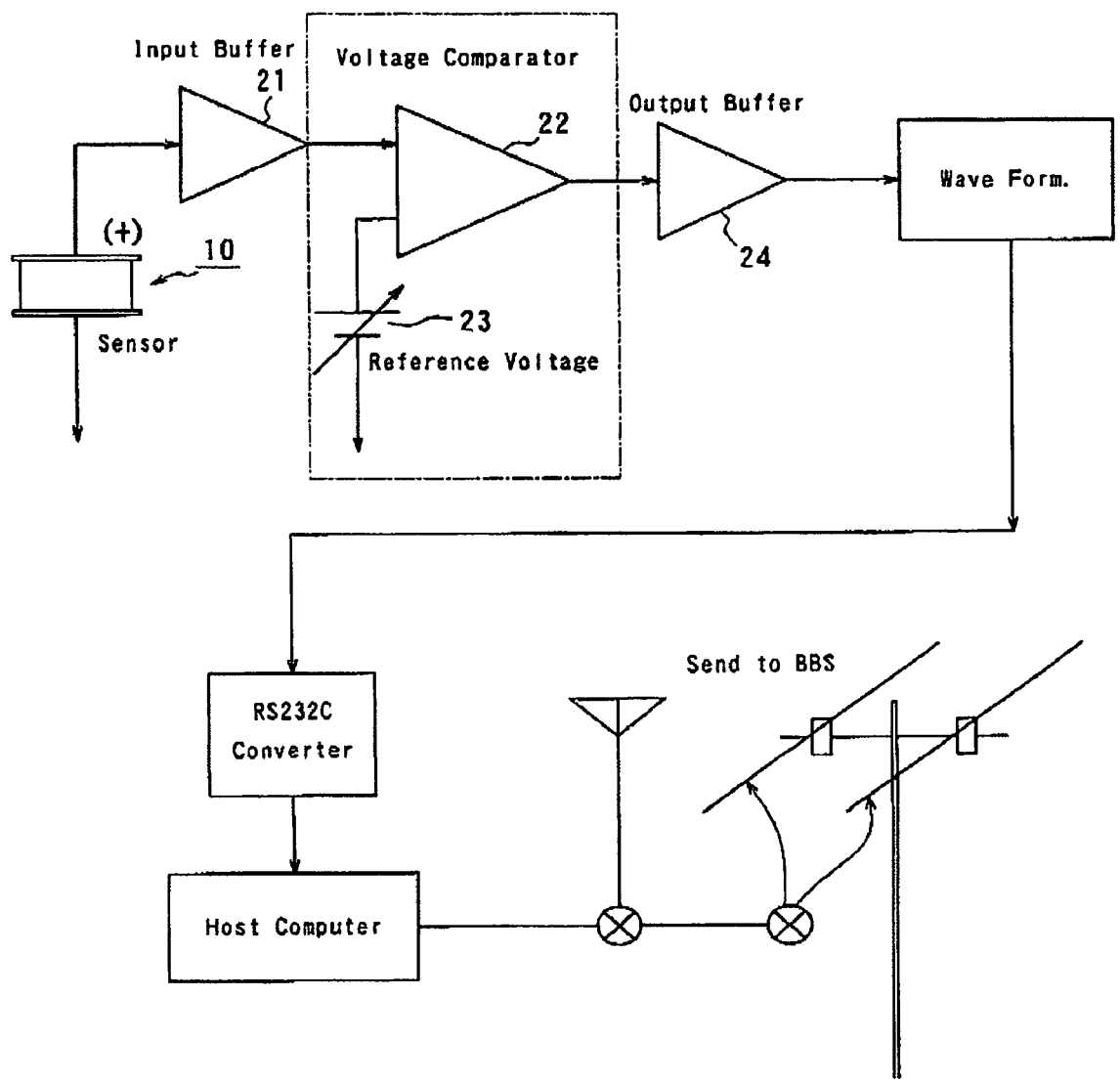
FIG. 13 is a block diagram of a hydrogen gas leak information transmitting system utilizing a hydrogen gas sensor according to the present invention.

FIGS. 11-13 are block diagrams of a hydrogen gas leak alarm system, a hydrogen gas leak controlling system and a hydrogen gas leak transmitting system which utilize hydrogen gas sensors according to the present invention.

FIG. 11 is a block diagram of the hydrogen gas leak alarm system utilizing the hydrogen gas sensor of the present invention. The electromotive force variation as a hydrogen gas detecting information from the hydrogen gas sensor 10 is input into an input buffer 21 of high input impedance, converted in impedance and signal level, and input into a voltage comparator 22. In the voltage comparator 22, the input signal is compared with the reference voltage of a standard power supply 23, and the thus obtained compared result is output via an output buffer 24 provided at the next stage, and input into an alarm buzzer or a light-emitting diode panel (not shown), thereby constituting the hydrogen gas leak alarm system.

FIG. 12 is a block diagram of the hydrogen gas leak controlling system utilizing the hydrogen gas sensor of the present invention. In the system, when hydrogen gas over a predetermined level is detected by the hydrogen gas sensor, the hydrogen gas leak information is known via a light-emitting diode panel and at the same time, an external relay or magnetic valve is operated.

The electromotive force variation as a hydrogen gas detecting information from the hydrogen gas sensor 10 is input into an input buffer 21 of high input impedance, converted in impedance and signal level, and input into a voltage comparator 22. In the voltage comparator 22, the input signal is compared with the reference voltage of a standard power supply 23, and the thus obtained compared result is output via an output buffer 24 provided at the next stage, and input into an alarm buzzer for warning hydrogen gas leak, a light-emitting diode panel (not shown) for displaying the hydrogen gas leak or an Exit Control System for operating an external relay or magnetic valve via a TTL OUT, thereby constituting the hydrogen gas leak alarm system.

FIG. 13 is a block diagram of the hydrogen gas leak transmitting system utilizing the hydrogen gas sensor of the present invention. In the system, when hydrogen gas over a predetermined level is detected by the hydrogen gas sensor, the hydrogen gas leak information is transmitted to a local area via a wireless LAN or a BBS by using a computer.

The electromotive force variation as a hydrogen gas detecting information from the hydrogen gas sensor 10 is input into an input buffer 21 of high input impedance, converted in impedance and signal level, and input into a voltage comparator 22. In the voltage comparator 22, the input signal is compared with the reference voltage of a standard power supply 23. The thus obtained compared result is output via an output buffer 24 provided at the next stage, converted in signal level (Wave Form), transmitted to a host computer via an RS232C port and the like as a typical serial communication of PC, and transmitted to a local area via a wireless LAN or a BBS.

Figure 14:
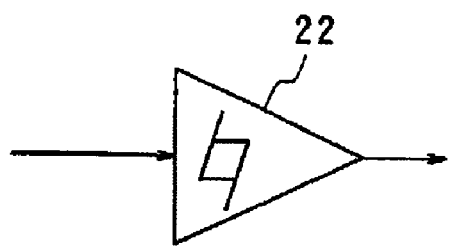
FIG. 14 is a schematic explanatory view of the structure and operation of the voltage comparator in the systems illustrated in FIGS. 11-13.
Figure 14:
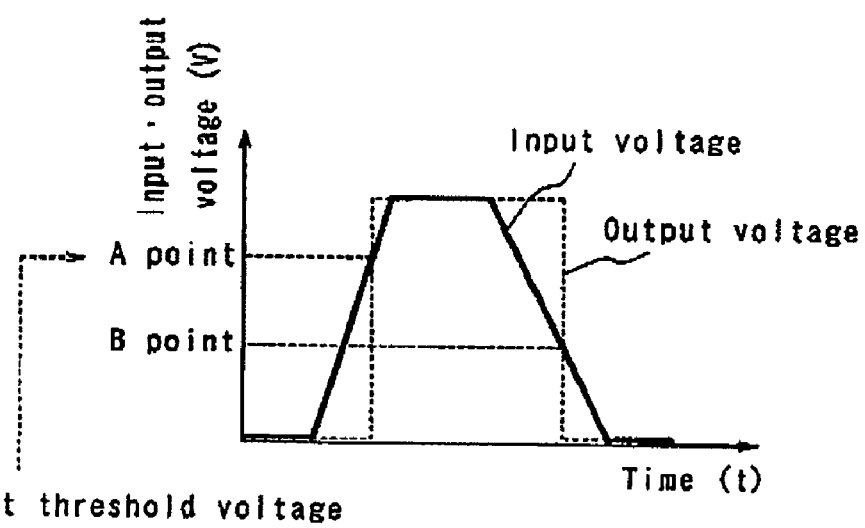

FIG. 14 is a schematic explanatory view of the structure and operation of the voltage comparator in the systems illustrated in FIGS. 11-13. The voltage comparator 22 is a most important component among all of the components of the systems. When a voltage over the reference voltage is output from the input buffer 21 and input into the voltage comparator 22, the output voltage of the voltage comparator 22, which is almost equal to the power supply voltage, is on, and when a voltage below the reference voltage is output from the input buffer 21 and input into the voltage comparator 22, the output voltage of the voltage comparator 22 is off (becomes almost zero) from on.

Conventionally, the voltage comparison would be carried out by using an exclusive IC installed in the voltage comparator. In the present invention, in contrast, in order to simplify the electric circuit construction and realize the absolute voltage comparison, a Shumitt inverter (Shumitt circuit) as a digital IC is installed in the voltage comparator. In this case, therefore, the voltage comparator is utilized as an analog voltage comparator by using the threshold voltage of the Shumitt circuit as a reference voltage standard.

Generally, the Shumitt inverter is used in a digital circuit for realizing digital functions such as waveform shaping of digital waveform with noise. In this embodiment, the digital functions of the Shumitt inverter are utilized as analog functions in the voltage comparator 22. In this point of view, the difference between the threshold voltages when the voltage comparator is on from off and off from on is utilized to determine the standard voltage in analog. Therefore, the external controlling circuit can not become unstable around the threshold voltage, thereby to be stabilized.

Moreover, since the threshold voltage of the Shumitt voltage corresponds to the reference standard voltage of the voltage comparator 22, the construction of the voltage comparator 22 can be simplified without an external standard voltage power supply and the operation of the voltage comparator 22 can be carried out stably and absolutely.

Figure 15:
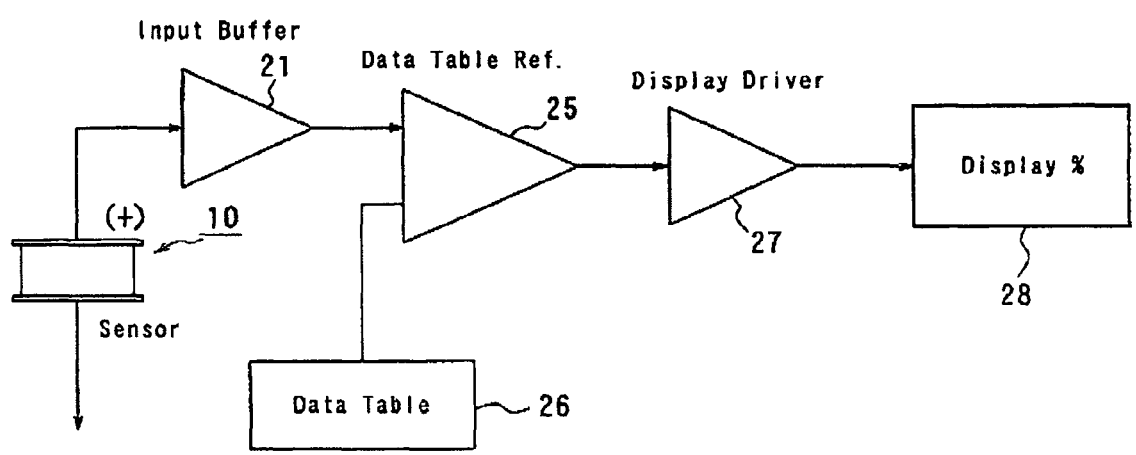
FIG. 15 is a block diagram of a hydrogen gas analyzer utilizing a hydrogen gas sensor according to the present invention.

FIG. 15 is a block diagram of a hydrogen gas analyzer utilizing a hydrogen gas sensor according to the present invention.

In the hydrogen gas analyzer illustrated in FIG. 15, the electromotive force as a hydrogen gas detecting information from the hydrogen gas sensor 10 is converted in impedance level and signal level by an input buffer 21 of higher input impedance, and input into a Data Table Reference circuit 25 provided at the next stage. In the Data Table Reference circuit 25 is input a Data Table 26 relating to the hydrogen gas concentrations and the electromotive forces of the hydrogen gas sensor, which the Data Table 26 is compared with an electromotive force input into the Data Table Reference circuit 25 to display the hydrogen gas concentration corresponding the input electromotive force via a Display Driver 27.

Figure 16:
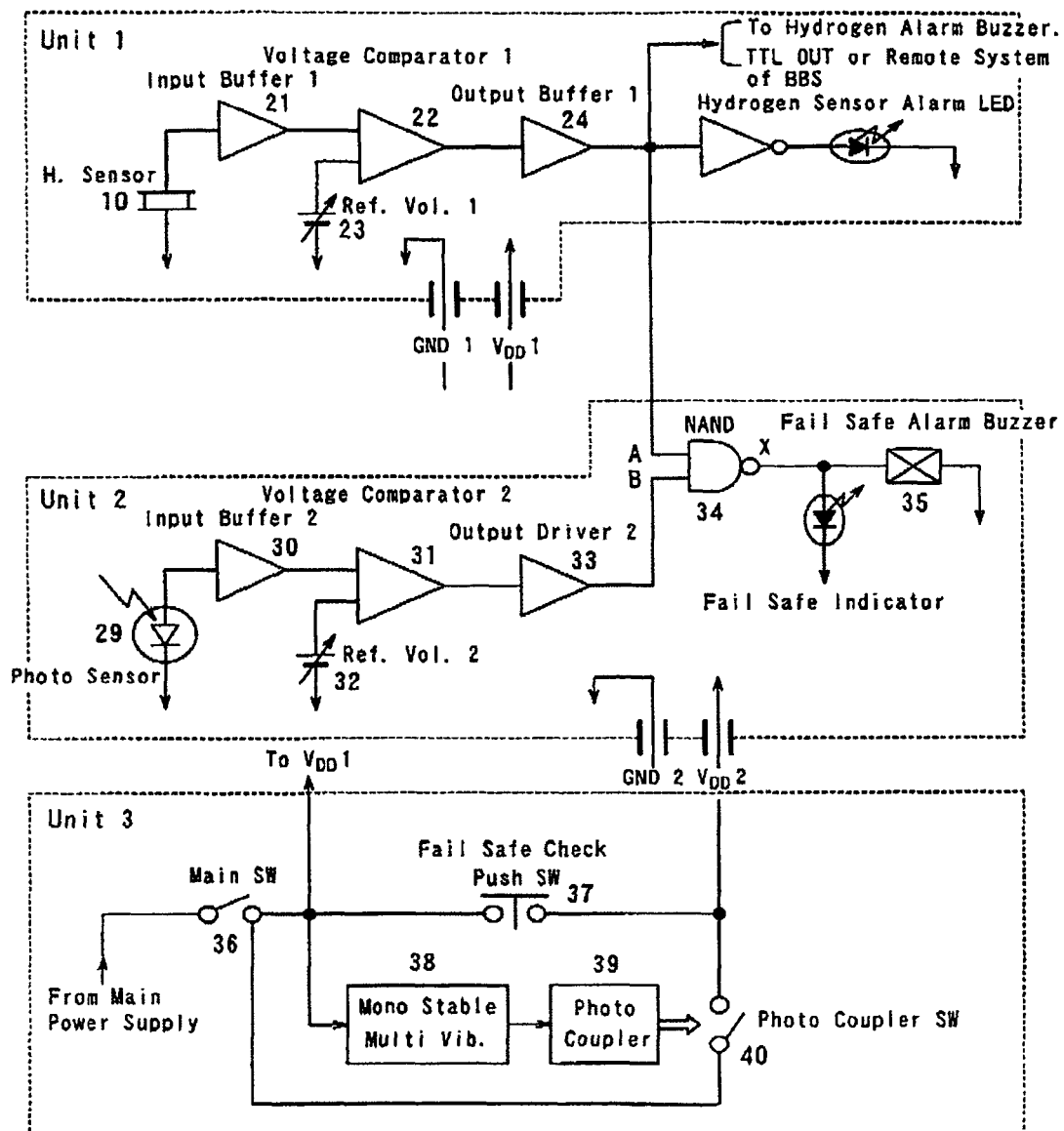
FIG. 16 is a block diagram of the hydrogen gas leak alarm system with Fail-Safe function.

FIG. 16 is a block diagram of the hydrogen gas leak alarm system with Fail-Safe function. In this embodiment, the Fail-Safe functions (units 2 and 3) are combined with the hydrogen gas leak alarm system (unit 1) or the like. In the unit 1, the electromotive force variation as a hydrogen gas detecting information from the hydrogen gas sensor 10 is input into an input buffer 21 of high input impedance, converted in impedance and signal level, and input into a voltage comparator 22. In the voltage comparator 22, the input signal is compared with the reference voltage of a standard power supply 23, and the thus obtained compared result is output to a logical operating circuit 34 via an output buffer 24 provided at the next stage.

In the unit 2, the Fail-Safe function is applied to the hydrogen gas sensor element, the input buffer and the voltage comparator. A photo sensor 29 is installed in the hydrogen gas sensor element and monitors the contamination of the sensor component of the hydrogen gas sensor element from external environment.

An information from the photo sensor 29 is input in an input buffer 30 of high input impedance, converted in impedance and signal level, and input in a voltage comparator 31. In the voltage comparator 31, the input signal is compared with the reference voltage of a standard power supply 32, and the thus obtained compared result is output to a logical operating circuit 34 via an Output Driver 33 provided at the next stage. In the logical operating circuit 34, the compared result relating to the input signal and the reference voltage is calculated, and an alarm buzzer 35 is switched off only when no hydrogen gas leak information is detected from the output buffer 24 and the operation of the photo sensor 29 is normal, that is, both of the output buffer 24 and the photo sensor 29 are stationary states. Except the stationary states of the output buffer 24 and the photo sensor 29, for example, when the hydrogen gas sensor 10 puts out a hydrogen gas detecting signal and/or the photo sensor 29 detects contamination from the external environment, the alarm buzzer 35 is switched on.

In the unit 3, the Fail-Safe function is applied to the light-emitting display for warning and the alarm buzzer. The operating conditions of the light-emitting display and the alarm buzzer are visually checked via a switch 37 for visual check or when the hydrogen gas leak alarm system is switched on.

Figure 17:
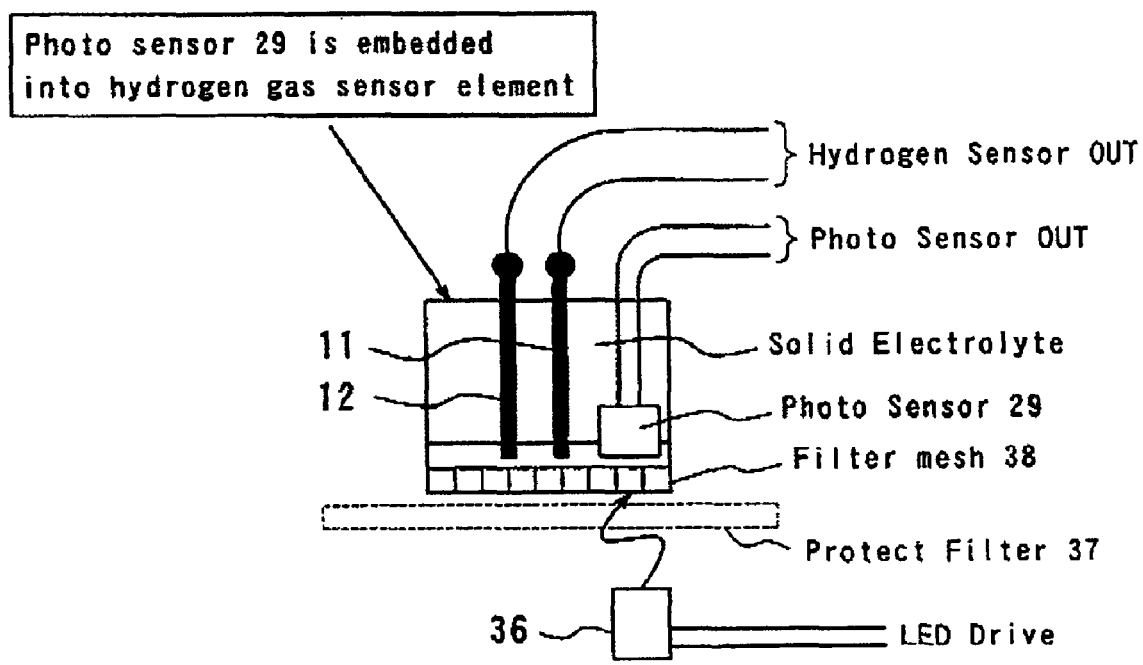
FIG. 17 is a schematic structural view of a hydrogen gas sensor element with Fail-Safe function.

FIG. 17 is a schematic structural view of a hydrogen gas sensor element with Fail-Safe function. The Fail-Safe function relating to the hydrogen gas leak alarm system can be applied to the hydrogen gas sensor detecting section by calculating the signal from the hydrogen gas detecting section at the logical operating circuit 34 via the units 2 and 3. The Fail-Safe function can be also applied to the logical operating circuit 34 via another circuit which is provided in parallel with the circuit 34.

In FIG. 17, the Fail-Safe function is applied to the hydrogen gas detecting section, and the LED signal from the LED 36 is transmitted via a protective mesh 37 and detected at the photo sensor 29 via a translucent mesh 38. When the translucent mesh 38 is contaminated from external environment and thus, shut down, the signal from the photo sensor 29 is off, so that the photo sensor 29 is shut down against hydrogen gas due to the contamination. Since the hydrogen gas sensor element functions as an active element with spontaneous electromotive force under non-hydrogen gas atmosphere, the operating condition of the sensor element can be monitored by detecting the spontaneous electromotive voltage.

Although the present invention was described in detail with reference to the above examples, this invention is not limited to the above disclosure and every kind of variation and modification may be made without departing from the scope of the present invention.

The invention claimed is:

1. A hydrogen gas sensor comprising a first electrode, a second electrode and an electrolyte contacting with said first electrode and said second electrode, said electrolyte being made of at least one of phosphorous tungsten acid and phosphorousmolybdenum acid and containing glass wool therein for enhancing a strength of said electrolyte and an adhesion for said first electrode and said second electrode, wherein said first electrode and second electrode are made or corresponding different materials in chemical potential for hydrogen gas, and said first electrode is made of higher chemical potential material and functions as a detecting electrode, and said second electrode is made of lower chemical potential material and functions as a standard electrode, wherein said hydrogen gas is detected on an electromotive force generated between said first electrode and said second electrode.

2. The hydrogen gas sensor as defined in claim 1, wherein said first electrode includes a first electrode material which exhibits a standard electromotive force of 0.8V or over in the cell of $H_2(-)|50$ mol/m$^3$ $H_2SO_4$|sample(+), and said second electrode includes a second electrode material which exhibits a standard electromotive force of less than 0.8V in the same cell construction.

3. The hydrogen gas sensor as defined in claim 2, wherein said first electrode material includes at least one selected from the group consisting of Pt, Pt alloy, Pd and Pd alloy, and said second electrode material includes at least one selected from the group consisting of Ni, Ni alloy, Ti, Ti alloy, Cu, Cu alloy, Fe, Fe alloy, Al, Al alloy and organic conductive material.

4. The hydrogen gas sensor as defined in claim 1, wherein said first electrode and said second electrode are shaped in plate and disposed so as to be opposed to one another, and said electrolyte is disposed between said first electrode and said second electrode.

5. The hydrogen gas sensor as defined in claim 1, wherein said first electrode and said second electrode are shaped in rod or line and disposed on an insulating substrate so as to be separated from one another, and said electrolyte is disposed between said first electrode and said second electrode.

6. The hydrogen gas sensor as defined in claim 1, wherein said second electrode is shaped in cylinder so that said first electrode is disposed in said second electrode, and said electrolyte is disposed at least partially in between said first electrode and said second electrode.

7. The hydrogen gas sensor as defined in claim 1, wherein said electrolyte is a solid electrolyte.

8. The hydrogen gas sensor as defined in claim 7, wherein said solid electrolyte is made of a solid electrolyte raw material and said glass wool, wherein said solid electrolyte is made through the solidification of said solid electrolyte raw material with said glass wool or the infiltration of said glass wool into said electrolyte raw material which is processed in porosity or mesh.

9. A hydrogen gas leak alarm system comprising a hydrogen gas sensor as defined in claim 1 and a voltage comparator, wherein an electromotive force variation as a hydrogen gas detecting information from said hydrogen gas sensor is compared with a reference voltage of said voltage comparator, thereby to put out an signal on the comparison of said electromotive force variation and said reference voltage.

10. The hydrogen gas leak alarm system as defined in claim 9, wherein said voltage comparator is configured such that a threshold voltage of a Shumitt inverter is defined as said reference voltage, and compared with an input voltage corresponding to said hydrogen gas detecting information, thereby to put out said signal.

11. A hydrogen gas leak controlling system comprising a hydrogen gas sensor as defined in claim 1 and a voltage comparator, wherein an electromotive force variation as a hydrogen gas detecting information from said hydrogen gas sensor is compared with a reference voltage of said voltage comparator, thereby to put out a signal on the comparison of said electromotive force variation and said reference voltage.

12. The hydrogen gas leak controlling system as defined in claim 11, wherein said voltage comparator is configured such that a threshold voltage of a Shumitt inverter is defined as said reference voltage, and compared with an input voltage corresponding to said hydrogen gas detecting information, thereby to put out said signal.

13. A hydrogen gas leak information transmitting system comprising a hydrogen gas sensor as defined in claim 1 and a voltage comparator, wherein an electromotive force variation as a hydrogen gas detecting information from said hydrogen gas sensor is compared with a reference voltage of said voltage comparator, thereby to put out a signal on the comparison of said electromotive force variation and said reference voltage.

14. The hydrogen gas leak information transmitting system as defined in claim 13, wherein said voltage comparator is configured such that a threshold voltage of a Shumitt inverter is defined as said reference voltage, and compared with an input voltage corresponding to said hydrogen gas detecting information, thereby to put out said signal.

15. A hydrogen gas sensor array comprising a plurality of hydrogen gas sensors as defined in claim 1, wherein said hydrogen gas sensors are arranged on the same substrate.

16. A hydrogen gas analyzer comprising a hydrogen gas sensor as defined in claim 1 and an electric circuit for detecting an electromotive force from said hydrogen gas sensor,
wherein hydrogen gas concentration is detected in dependence on the intensity of said electromotive force.

17. A hydrogen gas sensor comprising a first electrode, a second electrode and an electrolyte contacting with said first electrode and said second electrode, said electrolyte being made of at least one of phosphorous tungsten acid and phosphorousmolybdenum acid and containing glass wool therein for enhancing a strength of said electrolyte and an adhesion for said first electrode and said second electrode,
wherein said first electrode and said second electrode are made of corresponding different material in absorption-dissociation active degree for hydrogen gas, and said first electrode is made of higher absorption-dissociation material and functions as a detecting electrode, and said second electrode is made of lower absorption-dissociation material and functions as a standard electrode,
wherein said hydrogen gas is detected on an electromotive force generated between said first electrode and said second electrode.

18. The hydrogen gas sensor as defined in claim 17, wherein said first electrode includes a first electrode material which exhibits a standard electromotive force of 0.8V or over in the cell of $H_2(-)|50 \text{ mol/m}^3 \text{ } H_2SO_4|sample(+)$, and said second electrode includes a second electrode material which exhibits a standard electromotive force of less than 0.8V in the same cell construction.

19. The hydrogen gas sensor as defined in claim 18, wherein said first electrode material includes at least one selected from the group consisting of Pt, Pt alloy, Pd and Pd alloy, and said second electrode material includes at least one selected from the group consisting of Ni, Ni alloy, Ti, Ti alloy, Cu, Cu alloy, Fe, Fe alloy, Al, Al alloy and organic conductive material.

20. The hydrogen gas sensor as defined in claim 17, wherein said first electrode and said second electrode are shaped in plate and disposed so as to be opposed to one another, and said electrolyte is disposed between said first electrode and said second electrode.

21. The hydrogen gas sensor as defined in claim 17, wherein said first electrode and said second electrode are shaped in rod or wire and disposed on an insulating substrate so as to be separated from one another, and said electrolyte is disposed between said first electrode and said second electrode.

22. The hydrogen gas sensor as defined in claim 17, wherein said second electrode is shaped in cylinder so that said first electrode is disposed in said second electrode, and said electrolyte is disposed at least partially in between said first electrode and said second electrode.

23. The hydrogen gas sensor as defined in claim 17, wherein said electrolyte is a solid electrolyte.

24. The hydrogen gas sensor as defined in claim 17, wherein said solid electrolyte is made of a solid electrolyte raw material and said glass wool, wherein said solid electrolyte is made through the solidification of said solid electrolyte raw material with said glass wool or the infiltration of said glass wool into said electrolyte raw material which is processed in porosity or mesh.

25. A hydrogen gas leak alarm system comprising a hydrogen gas sensor as defined in claim 17 and a voltage comparator, wherein an electromotive force variation as a hydrogen gas detecting information from said hydrogen gas sensor is compared with a reference voltage of said voltage comparator, thereby to put out a signal on the comparison of said electromotive force variation and said reference voltage.

26. The hydrogen gas leak alarm system as defined in claim 25, wherein said voltage comparator is configured such that a threshold voltage of a Shumitt inverter is defined as said reference voltage, and compared with an input voltage corresponding to said hydrogen gas detecting information, thereby to put out said signal.

27. A hydrogen gas leak controlling system comprising a hydrogen gas sensor as defined in claim 17 and a voltage comparator, wherein an electromotive force variation as a hydrogen gas detecting information from said hydrogen gas sensor is compared with a reference voltage of said voltage comparator, thereby to put out a signal on the comparison of said electromotive force variation and said reference voltage.

28. The hydrogen gas leak controlling system as defined in claim 27, wherein such voltage comparator is configured such that a threshold voltage of a Shumitt inverter is defined as said reference voltage, and compared with an input voltage corresponding to said hydrogen gas detecting information, thereby to put out said signal.

29. A hydrogen gas leak information transmitting system comprising a hydrogen gas sensor as defined in claim 17 and a voltage comparator, wherein an electromotive force variation as a hydrogen gas detecting information from said hydrogen gas sensor is compared with a reference voltage of said voltage comparator, thereby to put out a signal on the comparison of said electromotive force variation and said reference voltage.

30. The hydrogen gas leak information transmitting system as defined in claim 29, wherein such voltage comparator is configured such that a threshold voltage of a Shumitt inverter is defined as said reference voltage, and compared with an input voltage corresponding to said hydrogen gas detecting information, thereby to put out said signal.

31. A hydrogen gas sensor array comprising a plurality of hydrogen gas sensors as defined in claim 17, wherein said hydrogen gas sensors are arranged on the same substrate.

32. A hydrogen gas analyzer comprising a hydrogen gas sensor as defined in claim 17 and an electric circuit for detecting an electromotive force from said hydrogen gas sensor,
wherein hydrogen gas concentration is detected in dependence on the intensity of said electromotive force.

33. A hydrogen gas sensor element comprising:
a hydrogen gas sensor comprising a first electrode, a second electrode and an electrolyte contacting with said first electrode and said second electrode, wherein said first electrode and second electrode are made of corresponding different materials in chemical potential for hydrogen gas, and said first electrode is made of higher chemical potential material and functions as a detecting electrode, and said second electrode is made of lower chemical potential material and functions as a standard electrode, wherein said hydrogen gas is detected on an electromotive force generated between said first electrode and said second electrode; and a photo sensor for detecting hydrogen gas shielding contamination from external environment through the detection of an optical signal from an external LED, whereby Fail-Safe function for enhancing reliability in hydrogen gas detection is applied to said hydrogen gas sensor element.

34. A hydrogen gas sensor element comprising:

a hydrogen gas sensor comprising a first electrode, a second electrode and an electrolyte contacting with said first electrode and said second electrode, wherein said first electrode and said second electrode are made of corresponding different material in absorption-dissociation active degree for hydrogen gas, and said first electrode is made of higher absorption-dissociation material and functions as a detecting electrode, and said second electrode is made of lower absorption-dissociation material and functions as a standard electrode, wherein said hydrogen gas is detected on an electromotive force generated between said first electrode and said second electrode; and a photo sensor for detecting hydrogen gas shielding contamination from external environment through the detection of an optical signal from an external LED, whereby Fail-Safe function for enhancing reliability in hydrogen gas detection is applied to said hydrogen gas sensor element.

* * * * *